United States Patent
Roehn et al.

(10) Patent No.: US 9,603,983 B2
(45) Date of Patent: Mar. 28, 2017

(54) CATHETER PUMP ARRANGEMENT AND FLEXIBLE SHAFT ARRANGEMENT HAVING A CORE

(75) Inventors: Daniel Roehn, Berlin (DE); Reiner Liebing, Potsdam (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 1286 days.

(21) Appl. No.: 13/261,256

(22) PCT Filed: Oct. 22, 2010

(86) PCT No.: PCT/EP2010/006588
§ 371 (c)(1),
(2), (4) Date: Jun. 21, 2012

(87) PCT Pub. No.: WO2011/047884
PCT Pub. Date: Apr. 28, 2011

(65) Prior Publication Data
US 2012/0265002 A1 Oct. 18, 2012

Related U.S. Application Data

(60) Provisional application No. 61/254,339, filed on Oct. 23, 2009.

(30) Foreign Application Priority Data

Oct. 23, 2009 (EP) .................................. 09 07 5475

(51) Int. Cl.
*A61M 1/10* (2006.01)
*A61M 1/12* (2006.01)
*F16C 1/00* (2006.01)

(52) U.S. Cl.
CPC .......... *A61M 1/101* (2013.01); *A61M 1/1034* (2014.02); *A61M 1/125* (2014.02); *F16C 1/00* (2013.01)

(58) Field of Classification Search
CPC .... A61M 1/101; A61M 1/1034; A61M 1/125; F16C 1/00
See application file for complete search history.

(56) References Cited

U.S. PATENT DOCUMENTS

| | | |
|---|---|---|
| 3,510,229 A | 5/1970 | Smith et al. |
| 3,568,659 A | 3/1971 | Karnegis |
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |

(Continued)

FOREIGN PATENT DOCUMENTS

| | | |
|---|---|---|
| CA | 1008330 A1 | 4/1977 |
| CA | 2311977 A1 | 12/2000 |

(Continued)

*Primary Examiner* — Amanda Patton
(74) *Attorney, Agent, or Firm* — White & Case LLP

(57) ABSTRACT

The invention relates to a flexible shaft arrangement having a flexible hollow shaft which has an end at the drive side and an end at the output side, wherein the hollow shaft is reinforced sectionally between these ends by a core extending in its interior. Stiffer and more flexible sections can hereby be selectively positioned within the shaft arrangement.

17 Claims, 2 Drawing Sheets

(56) References Cited

U.S. PATENT DOCUMENTS

| | | | |
|---|---|---|---|
| 4,215,703 A * | 8/1980 | Willson | A61M 25/09033 600/585 |
| 4,559,951 A | 12/1985 | Dahl et al. | |
| 4,563,181 A | 1/1986 | Wijayarathna et al. | |
| 4,676,249 A * | 6/1987 | Arenas | A61M 25/09025 600/434 |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A * | 6/1988 | Kensey | A61M 1/101 415/221 |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A | 11/1990 | Hwang et al. | |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A | 3/1992 | Schwartz et al. | |
| 5,097,849 A | 3/1992 | Kensey et al. | |
| 5,108,411 A | 4/1992 | McKenzie | |
| 5,112,292 A | 5/1992 | Hwang et al. | |
| 5,113,872 A | 5/1992 | Jahrmarkt et al. | |
| 5,117,838 A | 6/1992 | Palmer et al. | |
| 5,118,264 A | 6/1992 | Smith | |
| 5,145,333 A | 9/1992 | Smith | |
| 5,163,910 A | 11/1992 | Schwartz et al. | |
| 5,169,378 A | 12/1992 | Figuera | |
| 5,183,384 A | 2/1993 | Trumbly | |
| 5,191,888 A | 3/1993 | Palmer et al. | |
| 5,201,679 A | 4/1993 | Velte, Jr. et al. | |
| 5,275,580 A | 1/1994 | Yamazaki | |
| 5,300,112 A | 4/1994 | Barr | |
| 5,373,619 A | 12/1994 | Fleischhacker et al. | |
| 5,376,114 A | 12/1994 | Jarvik | |
| 5,405,383 A | 4/1995 | Barr | |
| 5,501,574 A | 3/1996 | Raible | |
| 5,531,789 A | 7/1996 | Yamazaki et al. | |
| 5,701,911 A | 12/1997 | Sasamine et al. | |
| 5,755,784 A | 5/1998 | Jarvik | |
| 5,776,190 A | 7/1998 | Jarvik | |
| 5,813,405 A | 9/1998 | Montano, Jr. et al. | |
| 5,820,464 A | 10/1998 | Parlato | |
| 5,820,571 A | 10/1998 | Erades et al. | |
| 5,851,174 A | 12/1998 | Jarvik et al. | |
| 5,882,329 A | 3/1999 | Patterson et al. | |
| 5,888,241 A | 3/1999 | Jarvik | |
| 5,938,672 A | 8/1999 | Nash | |
| 6,007,478 A | 12/1999 | Siess et al. | |
| 6,030,397 A | 2/2000 | Monetti et al. | |
| 6,129,704 A | 10/2000 | Forman et al. | |
| 6,152,693 A | 11/2000 | Olsen et al. | |
| 6,168,624 B1 | 1/2001 | Sudai | |
| 6,254,359 B1 | 7/2001 | Aber | |
| 6,302,910 B1 | 10/2001 | Yamazaki et al. | |
| 6,308,632 B1 | 10/2001 | Shaffer | |
| 6,336,939 B1 | 1/2002 | Yamazaki et al. | |
| 6,346,120 B1 | 2/2002 | Yamazaki et al. | |
| 6,387,125 B1 | 5/2002 | Yamazaki et al. | |
| 6,503,224 B1 | 1/2003 | Forman et al. | |
| 6,506,025 B1 | 1/2003 | Gharib | |
| 6,508,787 B2 | 1/2003 | Erbel et al. | |
| 6,517,315 B2 | 2/2003 | Belady | |
| 6,527,521 B2 | 3/2003 | Noda | |
| 6,533,716 B1 | 3/2003 | Scmitz-Rode et al. | |
| 6,537,030 B1 | 3/2003 | Garrison | |
| 6,537,315 B2 | 3/2003 | Yamazaki et al. | |
| 6,592,612 B1 | 7/2003 | Samson et al. | |
| 6,652,548 B2 | 11/2003 | Evans et al. | |
| 6,719,791 B1 | 4/2004 | Nusser | |
| 6,726,568 B2 * | 4/2004 | Tanaka | A61B 8/12 464/52 |
| 6,860,713 B2 | 3/2005 | Hoover | |
| 6,945,977 B2 | 9/2005 | Demarais et al. | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,074,018 B2 | 7/2006 | Chang | |
| 7,179,273 B1 | 2/2007 | Palmer et al. | |
| 7,393,181 B2 | 7/2008 | McBride et al. | |
| 7,467,929 B2 | 12/2008 | Nusser et al. | |
| 7,731,675 B2 | 6/2010 | Aboul-Hosn et al. | |
| 7,828,710 B2 | 11/2010 | Shifflette | |
| 7,927,068 B2 | 4/2011 | McBride et al. | |
| 7,934,909 B2 | 5/2011 | Neusser et al. | |
| 2002/0123661 A1 | 9/2002 | Verkerke et al. | |
| 2003/0135086 A1 | 7/2003 | Khaw et al. | |
| 2003/0231959 A1 | 12/2003 | Snider | |
| 2004/0044266 A1 | 3/2004 | Siess et al. | |
| 2004/0046466 A1 | 3/2004 | Siess et al. | |
| 2004/0093074 A1 | 5/2004 | Hildebrand et al. | |
| 2004/0215222 A1 | 10/2004 | Krivoruchko | |
| 2004/0215228 A1 | 10/2004 | Simpson et al. | |
| 2006/0008349 A1 | 1/2006 | Khaw | |
| 2006/0062672 A1 | 3/2006 | McBride et al. | |
| 2006/0195004 A1 | 8/2006 | Jarvik | |
| 2008/0132747 A1 | 6/2008 | Shifflette | |
| 2008/0262584 A1 | 10/2008 | Bottomley et al. | |
| 2008/0306327 A1 | 12/2008 | Shifflette | |
| 2009/0060743 A1 | 3/2009 | McBride et al. | |
| 2009/0082723 A1 | 3/2009 | Krogh et al. | |
| 2009/0093764 A1 | 4/2009 | Pfeffer et al. | |
| 2009/0093796 A1 | 4/2009 | Pfeffer et al. | |
| 2010/0041939 A1 | 2/2010 | Siess | |
| 2010/0268017 A1 | 10/2010 | Siess | |
| 2011/0238172 A1 | 9/2011 | Akdis | |
| 2011/0275884 A1 | 11/2011 | Scheckel | |
| 2012/0039711 A1 | 2/2012 | Roehn | |
| 2012/0041254 A1 | 2/2012 | Scheckel | |
| 2012/0046648 A1 | 2/2012 | Scheckel | |
| 2012/0093628 A1 | 4/2012 | Liebing | |
| 2012/0101455 A1 | 4/2012 | Liebing | |
| 2012/0142994 A1 | 6/2012 | Toellner | |
| 2012/0184803 A1 | 7/2012 | Simon et al. | |
| 2012/0224970 A1 | 9/2012 | Schumacher et al. | |
| 2012/0234411 A1 | 9/2012 | Scheckel | |
| 2012/0237353 A1 | 9/2012 | Schumacher et al. | |
| 2012/0237357 A1 | 9/2012 | Schumacher et al. | |
| 2012/0264523 A1 | 10/2012 | Liebing | |
| 2012/0265002 A1 | 10/2012 | Roehn et al. | |
| 2012/0294727 A1 | 11/2012 | Roehn | |
| 2012/0301318 A1 | 11/2012 | Er | |
| 2012/0308406 A1 | 12/2012 | Schumacher | |
| 2013/0019968 A1 | 1/2013 | Liebing | |
| 2013/0041202 A1 | 2/2013 | Toellner | |
| 2013/0060077 A1 | 3/2013 | Liebing | |
| 2013/0066139 A1 | 3/2013 | Wiessler et al. | |
| 2013/0085318 A1 | 4/2013 | Toellner | |
| 2013/0177409 A1 | 7/2013 | Schumacher et al. | |
| 2013/0177432 A1 | 7/2013 | Toellner | |
| 2013/0204362 A1 | 8/2013 | Toellner | |
| 2013/0237744 A1 | 9/2013 | Pfeffer et al. | |
| 2014/0039465 A1 | 2/2014 | Schulz et al. | |

FOREIGN PATENT DOCUMENTS

| | | |
|---|---|---|
| CA | 2701809 A1 | 4/2009 |
| CA | 2701810 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 2908143 A1 | 9/1979 |
| DE | 4124299 A1 | 1/1992 |
| DE | 42 08 221 A1 | 9/1993 |
| DE | 69103295 T2 | 12/1994 |
| DE | 19535781 A1 | 3/1997 |
| DE | 19711935 A1 | 4/1998 |
| DE | 69407869 T2 | 4/1998 |

(56) References Cited

FOREIGN PATENT DOCUMENTS

| | | |
|---|---|---|
| DE | 29804046 U1 | 6/1998 |
| DE | 69017784 T3 | 4/2000 |
| DE | 199 62 073 A1 | 7/2001 |
| DE | 69427390 T2 | 9/2001 |
| DE | 101 13 208 A1 | 10/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0 916 359 A1 | 5/1999 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| FR | 1 418 339 A | 11/1965 |
| GB | 562 156 A | 6/1944 |
| GB | 2 015 699 A | 9/1979 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 | 10/2000 |
| WO | 0107760 A1 | 2/2001 |
| WO | 0107787 A1 | 2/2001 |
| WO | 0183016 A2 | 11/2001 |
| WO | 03057013 A2 | 7/2003 |
| WO | 03103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | WO 2007/057132 A1 | 5/2007 |
| WO | 2007103390 A2 | 9/2007 |
| WO | 2007103464 A2 | 9/2007 |
| WO | 2007112033 A2 | 10/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

* cited by examiner

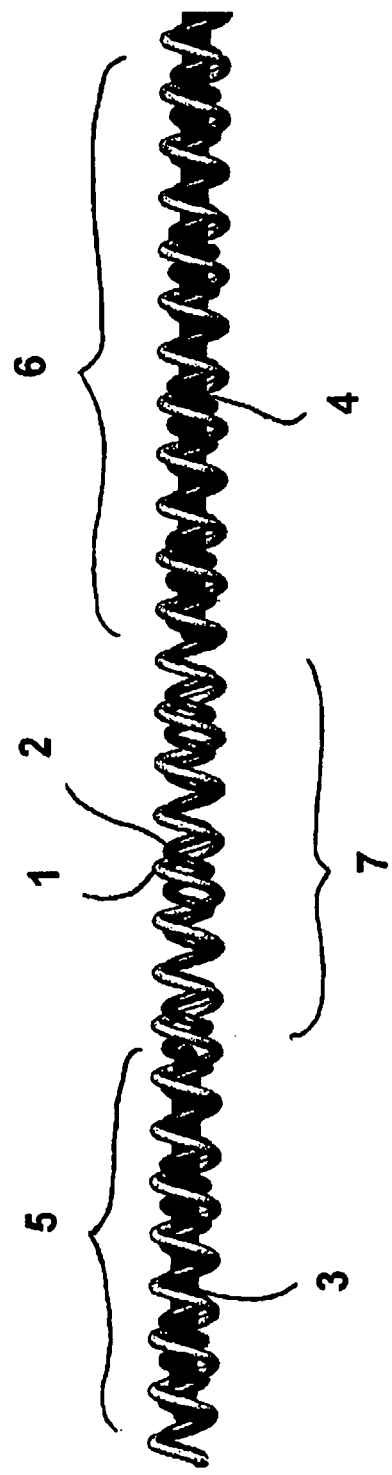
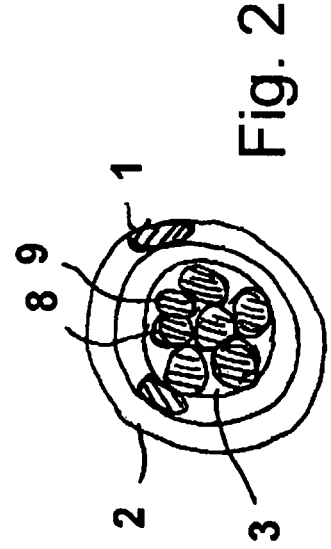
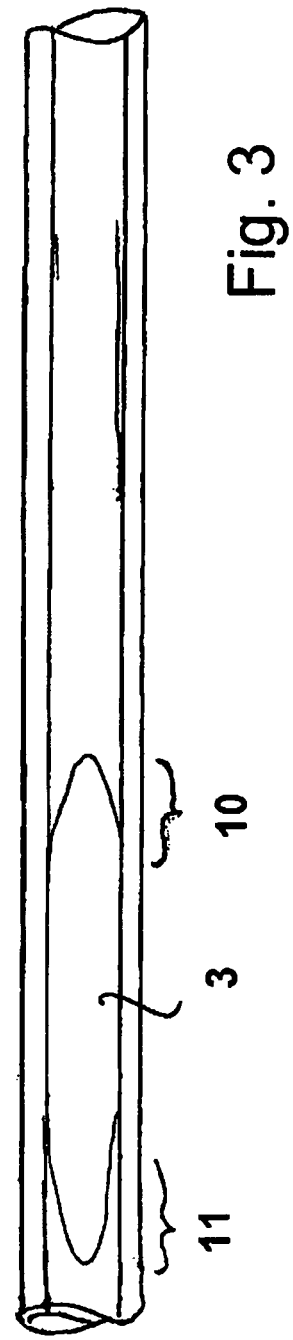

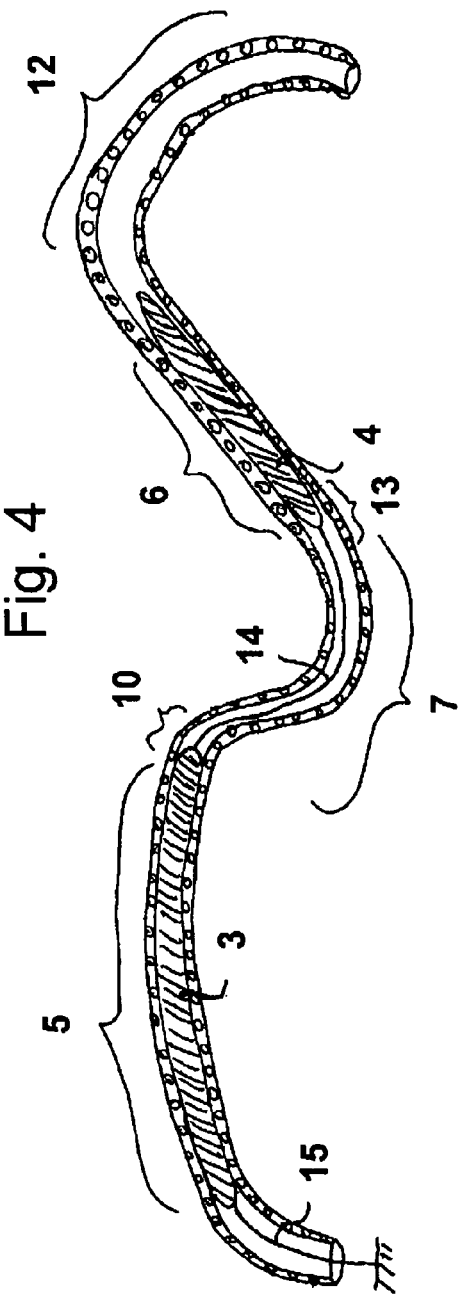
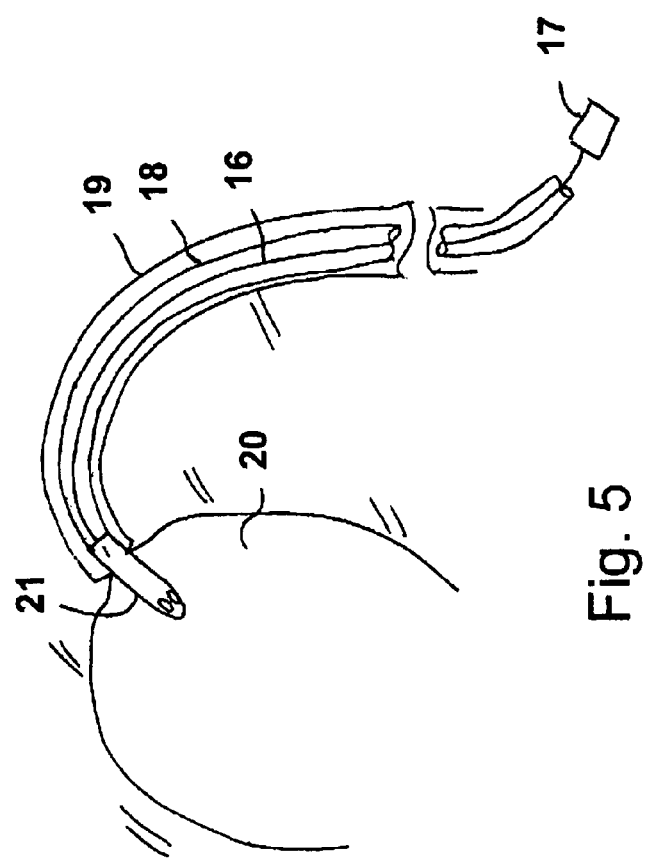
Fig. 4
Fig. 5

CATHETER PUMP ARRANGEMENT AND FLEXIBLE SHAFT ARRANGEMENT HAVING A CORE

BACKGROUND OF THE INVENTION

The invention is in the field of mechanical engineering and specifically relates to the transfer of movements and of torques via flexible shafts.

Flexible shafts of this type allow the transfer of torques for certain applications, for example to points which are difficult to access, e.g. for do-it-yourself (DIY) machinery or for dental applications where machining tools have to be introduced into the mouth of a patient. Small flexible shafts are generally suitable for use in the medical area, for example also for the drive of micropumps such as heart catheter pumps which are introduced into a body for the conveying of the body's own fluids, or for use in micromillers which can be used for removing tissue or deposits.

Various problems are known in the operation of such flexible shafts, in particular at high speeds, with one of these problems comprising the fact that a high noise development can arise due to imbalance or other mechanical irregularities, on the one hand, and also mechanical knocking can arise with high wear resulting therefrom. In addition, a torque has to be transferred which is as high as possible with a low mass of the shaft with a diameter of such flexible shafts which is as small as possible, which is difficult to bring into line with the desire for bending radii which are as tight as possible.

Different proposals are known from the prior art for the further development of such flexible shafts. It can, for example, be seen from the German laying-open publication DE 101 13 208 A1 that with a hollow shaft which is present in the form of a wound resilient coil, individual windings can be omitted to vary the stiffness of the shaft over the length. A better bending capability overall should thereby be achieved and, in addition, irregular rotations and vibrations should be avoided.

A hollow shaft which comprises two spring wire coils wound in opposite senses and can transfer torque in both directions of rotation is generally known from the laying-open publication DE 42 08 221 A1.

A shaft is known from the laying-open publication DE 29 08 143 which is wound from monofil strands and has a constant stiffness over its length.

U.S. Pat. No. 5,108,411 discloses a shaft which is divided into different portions with respect to its length, at least one of said portions having a structure in the manner of a hollow shaft, with a solid shaft portion being connected to the hollow-shaft portion. It is achieved in this manner that the shaft is divided into flexible and less flexible longitudinal portions. The more flexible shaft portions in this respect comprise a coil-type hollow shaft wound with double layers in opposite senses.

A flexible shaft for rotating operation is known from US 2008/0306327 which comprises in order to influence the vibration behavior either different segments arranged in a row after one another, a strand-type element with reinforcement sleeves mounted on the outside or a wound coil having mechanical properties changeable over the length. Reinforcements inserted inwardly into a hollow shaft are also mentioned there.

BRIEF SUMMARY OF THE INVENTION

It is the underlying object of the present invention against the background of the prior art to provide a heart catheter pump arrangement having a shaft arrangement as well as a flexible shaft arrangement with the least possible construction means, said shaft arrangement providing resistance to a mechanical build-up of vibrations and knocking of the shaft and also corresponding noise development.

The object is achieved in accordance with the invention by the features of claim 1. In this respect, provision is made with regard to a flexible shaft arrangement that the shaft arrangement has a throughgoing flexible shaft which has at least one hollow space between an end at the drive side and an end at the output side, wherein the shaft is sectionally reinforced by a core extending in the hollow space.

The flexibility of the shaft arrangement in the sections reinforced by the core is smaller than in the sections not reinforced by the core and, accordingly, on a bending load, no small bending radii can be achieved in the portions with a core. This is balanced by the fact that the stiffness and the stability of the shaft arrangement are improved in these regions. Since the positioning of the hollow shaft sections in which a core extends allows the reinforced sections to be selected/positioned freely, a design can be achieved with the shaft arrangement which, in accordance with the requirements in the specific case of use, achieves a stiffer shaft profile at the desired points than at other points and allows high bends, i.e. small bending radii, in specific other sections.

Provision is moreover made that the core sections are held in the interior of the hollow shaft by at least one axial spacer. Said spacer can fix the spacing of the respective core section from the end of the hollow shaft or from the shaft arrangement respectively and/or can also fix the spacing between two core sections.

The respective spacer advantageously has a smaller diameter than the core. It is thereby ensured that the spacer(s) do not contribute to an unwanted stiffening of the shaft arrangement in the regions in which no reinforcement by a core is provided.

The spacers can particularly advantageously be made as one or more flexible, strand-type bodies, for example as a wire, chain, rope or thread. They can comprise an in particular biocompatible plastic, a natural product or a metal such as steel. In this case, it is also sensible that the thread is fastened at both ends of the shaft arrangement and that individual core sections are fixed in the axial direction on the thread. The thread itself does not transfer any torque and nor does it contribute to the stiffness of the shaft arrangement.

The desired stiffness and flexibility can thus be adopted section-wise in the shaft arrangement as desired. The positioning of the stiffened parts of the flexible shaft arrangement can be adapted in the short term on the use of the shaft arrangement by the positioning of individual core sections on a thread.

One or more sections can be provided along the shaft arrangement, with a core being arranged in each and with the cores being axially spaced apart from one another. Respective core sections of the same type or also different core sections can be provided in the sections reinforced by a core.

Each of the core sections can have a stiffness section along its length, for example at least one end at which the respective core becomes more flexible to an increasing degree. A kinking of the hollow-formed parts of the shaft beyond the end of a core is thereby avoided and the stiffness section is stabilized. The shaft can in this respect also be made completely as a hollow shaft.

Provision can advantageously be made in this respect that the core rotates with the shaft in the region over which said core extends.

The respective core can fit into the hollow shaft section with an exact fit so that the bending force transfer also takes place directly and the core thus already absorbs forces with large bending radii. In this case, it is sensible if the respective core rotates with the shaft so as not to produce any friction losses.

In this respect, the core or the respective core section can also transfer torques. It is sensible for this purpose to provide a connection between the hollow shaft sections and the core which is as rotationally fixed as possible. The core can be pressed into the hollow shaft for this purpose.

The individual core or the individual core section can advantageously be manufactured from a plurality of strand elements by stranding. The thickness and the bendability of the core can thus be set as desired by this type of manufacture and the core becomes largely elastically deformable. The individual strand elements can advantageously be made as wires. The manufacture of the core thus becomes simple and inexpensive.

The shaft can in turn be made as a hollow shaft in the form of at least one wound helical sprint. Such a helical spring can, for example, be wound so tightly that the windings directly contact one another. Such a hollow shaft is very flexible and can nevertheless transfer torque.

With a hollow shaft of this kind, no material deformation which is too strong takes place during a very fast rotational movement, either, so that the heat development and the deforming work to be carried out on the rotation remain limited. Since a helical spring wound in one sense transfers a torque better in one direction than in the opposite direction of rotation, it can be advantageous that the hollow shaft is made of two coaxial helical screws wound in opposite senses and nesting in one another. In this case, one of the helical springs transfers the torque ideally in a first rotational sense, whereas the other helical spring transfers the torque ideally in the opposite rotational sense. A high flexibility with respect to bending operations nevertheless results. The two helical springs can be nested in one another such that the larger helical spring surrounds the smaller helical spring directly in a pressed seat. The mechanical clearance is thus minimized both in the axial direction and in the rotational direction.

The core can advantageously be fastened to the hollow shaft section at least one position in the interior thereof. A displacement of the core in the axial direction is thus reliably prevented. The connection can, for example, be established by soldering or welding.

Provision can advantageously be made in the shaft arrangement in accordance with the invention that the shaft arrangement has a distal end at the output side for connection of a drivable unit and a proximal end at the drive side for connection to a motor and that a coreless hollow shaft section is provided adjacent to the distal end.

Such a design is in particular of advantage when the distal end should be bent particularly highly and with a low resistance, for example for medical applications in which the actual unit is situated at the head of a catheter and thus at the distal end of the shaft arrangement and has accordingly to be handled as flexibly as possible. For example, a heart pump can be arranged at the end of the shaft arrangement which has to be led through an aortic arch.

The proximal regions of the shaft arrangement can then be relatively stiff since they are conducted through blood vessels extending in a stretched manner. A certain stiffness of the shaft arrangement is more important than the flexibility in these regions.

Provision can, however, also advantageously be made to make the distal end region (at the output side), in particular the region directly adjacent to a connected unit to be driven, for example at least the last 1%, 5% or 10% of the length of the shaft, stiffer than the average of the total length of the shaft or at least starting from this region to reduce the stiffness of the shaft continuously or abruptly toward the proximal end.

A good true run is thus achieved in the end region.

In this case, the shaft arrangement has a hollow catheter which surrounds the hollow shaft to protect the shaft arrangement as a whole and to isolate it from external influences. A coolant and a lubricant for the shaft can, for example, be provided in the interior of the hollow shaft.

A particularly advantageous medical application of the invention provides the equipping of a heart catheter pump arrangement with a flexible shaft arrangement in accordance with the above description.

Provision is made with respect to a heart catheter pump arrangement having a blood pump and having a shaft arrangement with a flexible fast-rotating shaft having an end at the drive side and an end at the output side and an unchanging outer diameter between the ends that the shaft has different orders of stiffness and/or flexibility by additional reinforcement bodies in at least two different axial sections contiguous in one piece.

This can be realized, for example, in that the stiffness of the shaft reduces in at least one step or continuously from the end region which is adjacent to the pump head and/or to the pump rotor at the end at the output side toward the proximal end of the shaft.

The stiffness is understood in this respect as the resistance which is opposed to a bending of the shaft. The flexibility also includes the property of the shaft to be bendable at all below a certain bending radius.

Different stiffnesses/flexibilities can be realized by different cross-sections of the shaft, different material property or the reinforcement by reinforcement elements inserted into the shaft. Such reinforcement elements can, for example, be inserted section-wise into a hollow shaft.

BRIEF DESCRIPTION OF THE DRAWINGS

The invention will be shown and subsequently described in the following with reference to an embodiment in a drawing.

There are shown

FIG. 1 a shaft arrangement in accordance with the invention in a three-dimensional representation having a plurality of sections reinforced by a core;

FIG. 2 a cross-section of the shaft arrangement of FIG. 1;

FIG. 3 a further embodiment of the shaft arrangement in a schematic representation;

FIG. 4 an embodiment of the shaft arrangement in accordance with the invention in bent form; and FIG. 5 the use of the shaft arrangement in accordance with the invention in a heart pump.

DETAILED DESCRIPTION OF THE INVENTION

FIG. 1 shows, in a three-dimensional view, a hollow shaft which comprises two helical screws 1, 2 which are wound in opposite senses and of which the first is shown as light and the second as dark. The winding in opposite senses of the two helical springs has the effect that one of the springs is compressed and the other is stretched in each direction of rotation. There is thus no deformation overall in the axial direction in dependence on the direction of rotation which is to be transferred.

The density of the windings of the individual springs and the thickness of the spring wire determine, on the one hand, the flexibility or stiffness respectively of the hollow shaft and, on the other hand, the torque which can be transferred.

Two core sections 3, 4 are furthermore shown in FIG. 1 which each stiffen the shaft arrangement in the axial sections 5, 6. The hollow shaft remains free in the axial section lying therebetween and is correspondingly more flexible there.

The core sections 3, 4 can be made as solid bodies, for example as plastic bodies or metal bodies, which have a high spring elasticity and break resistance as well as a high resistance to fatigue.

The core sections can, however, also be stranded cores which then comprise a plurality of strand elements, for example wires. This embodiment is shown in more detail in FIG. 2 where a section shows the radial arrangement of the two helical springs 1, 2 and of the core 3. It is also shown there that the core 3 comprises a plurality of strand elements 8, 9, whereby it becomes very flexibly and permanently deformable.

The two helical springs 1, 2 are dimensioned and arranged such that they are assembled radially into one another and coaxially to one another in a press fit so that a distribution of the torque to be transferred takes place between them. In addition, bending loads are also taken up together by both helical springs. The corresponding loads are likewise taken up in the sections in which a core is located within the hollow space of the helical springs 1, 2 by said core since it fits tightly in the hollow space.

It is shown with reference to FIG. 3 that the core sections each have an end converging to a taper, whereby the end region 10, 11 of the core 3 becomes more and more flexible toward the end. The stiffness is thereby not reduced abruptly to the degree of stiffness of the hollow shaft toward the end of each core section in the total observation of the shaft arrangement, but a constant transition rather takes place which results in a continuous distribution on a bending strain of the shaft arrangement to reduce the kinking strains and to reduce the risk of a tearing of the shaft arrangement.

The result is, with a given bending strain, that the bending radius is considerably increased in those sections 5, 6 in which the hollow shaft is reinforced by a core or by a core section. A substantially smaller bending radius is achieved in those sections in which no core is present. The above-described design of the end region of the core sections is suitable to avoid kinks between these regions.

In FIG. 4, a bent shaft arrangement in accordance with the invention is shown by way of example, with two cores 3, 4 being shown in sections 5, 6 which extend almost straight or have a large bending radius. The hollow shaft arrangement is particularly bent in the section 7, as it is in section 12.

The general transition of the stiffness by a corresponding design of the ends of the cores 3, 4 in the regions 10, 13 has the effect that the risk of kinking is reduced.

Spacers are shown by way of example between the cores 3, 4 in FIG. 4, just as between the core 3 and the end of the shaft arrangement at the drive side. The spacers are labeled by 14, 15 and can be made as more or less stiff, thin cores which have a substantially smaller diameter than the cores 3, 4, and equally a substantially smaller stiffness. The spacers 14, 15 can, however, simply be made only as a thread with negligible stiffness, with it being expedient in this case to fasten the spacers suitably at both ends of the hollow shaft arrangement to be able to keep the core sections 3, 4 tensioned as on a chain and to be able to keep them stable at preset spacings.

This embodiment has the advantage that, depending on the demands on the distribution of different stiffnesses along the hollow shaft arrangement, a series of cores/core sections can be drawn into the existing hollow shaft with spacers, with the length of the individual spacers being individually adaptable in accordance with the purpose of the shaft arrangement.

FIG. 5 schematically shows an application for the shaft arrangement in accordance with the invention, with the shaft arrangement there only being shown schematically and being labeled by 16. The shaft arrangement 16 is connected to a motor 17 at the drive side and extends in a hollow catheter 18 which can be introduced into a blood vessel 19 of a body, for example a human body, and can be introduced into a ventricle 20 via the path of this blood vessel.

A heart pump 21 is located at the end of the hollow catheter 18 and is made as an axial pump and has a rotor in its interior which can be driven by means of the shaft arrangement 16 at high speeds, for example between 10,000 and 20,000 revolutions per minute.

The advantages of the shaft arrangement in accordance with the invention are shown in that, on the one hand, the shaft arrangement can be easily inserted through the blood vessel 19 due to suitable stiff regions, but that in the distal region, viewed from the introduction point, that is in the region of the aortic arch toward the ventricle, a high flexibility of the shaft arrangement is given so that the heart pump 21 can be introduced into the ventricle there without the stiffness of the shaft arrangement or of the hollow catheter being able to result in injuries to the ventricle walls or to the aorta in the region of the aortic arch. A knocking of the shaft and acoustic resonance are reliably avoided by the suitable distribution of the core(s) along the shaft arrangement.

The invention claimed is:

1. A flexible drive shaft arrangement having a flexible drive shaft with an end at the drive side and an end at the output side, wherein the drive shaft has at least one hollow space between the end at the drive side and the end at the output side and is reinforced sectionally by a reinforcement body in the form of a core extending in a hollow space, wherein the at least one core is held in the interior of the drive shaft by at least one axial spacer, and wherein the core is configured to rotate with the drive shaft.

2. The flexible drive shaft arrangement in accordance with claim 1, wherein the at least one axial spacer has a smaller diameter than the core.

3. The flexible drive shaft arrangement in accordance with claim 2, wherein the at least one spacer is made as a flexible, stranded thread.

4. The flexible drive shaft arrangement in accordance with claim 1, wherein the core transfers torque in the hollow space in which it extends.

5. The flexible drive shaft arrangement in accordance with claim 1, wherein the core is comprised of a plurality of strand elements.

6. The flexible drive shaft arrangement in accordance with claim 5, wherein the strand elements are formed by wires.

7. The flexible drive shaft arrangement in accordance with claim 1, wherein the drive shaft is made at least section-wise as at least one wound helical spring.

8. The flexible drive shaft arrangement in accordance with claim 7, wherein the drive shaft has at least two coaxial screws wound in opposite senses and nested in one another.

9. The flexible drive shaft arrangement in accordance with claim 1, wherein the drive shaft is penetrated by a core in at least two axial regions spaced apart from one another.

10. The flexible drive shaft arrangement in accordance with claim 1, wherein the at least one core is fastened to the drive shaft in the interior thereof.

11. The flexible drive shaft arrangement in accordance with claim 1, wherein the drive shaft arrangement has a distal end at the output side for connection of a drivable unit and a proximal end at the drive side for the connection to a motor; and in that a coreless section of the drive shaft is provided adjacent to the distal end.

12. The flexible drive shaft arrangement in accordance with claim 10, wherein a distal end region at the drive side is made stiffer than the average of the total length of the drive shaft.

13. The flexible drive shaft arrangement in accordance with claim 1, wherein a hollow catheter for medical applications surrounding the drive shaft.

14. The flexible drive shaft arrangement in accordance with claim 13, wherein the drive shaft arrangement is for a heart catheter pump.

15. The flexible drive shaft arrangement in accordance with claim 14, wherein the stiffness of the drive shaft reduces in at least one step or continuously from the end region which is adjacent to the pump head and/or to the pump rotor toward the proximal end of the drive shaft.

16. The flexible drive shaft arrangement in accordance with claim 12, wherein the distal end region at the drive side directly adjacent to a connected unit to be driven is made stiffer than the average of the total length of the drive shaft.

17. The flexible drive shaft arrangement in accordance with claim 16, wherein the last 1%, 5% or 10% of the length of the drive shaft is made stiffer than the average of the total length of the drive shaft.

* * * * *